United States Patent [19]

Zirino et al.

[11] 4,058,446
[45] Nov. 15, 1977

[54] ANODIC STRIPPING VOLTAMMETRY SYSTEM AND COMBINATION ELECTRODE ASSEMBLY THEREFORE

[75] Inventors: Alberto Zirino; Cesar Clavell, both of San Diego, Calif.; Kent Huey, Anchorage, Alaska

[73] Assignee: The United States of America as represented by the Secretary of the Navy, Washington, D.C.

[21] Appl. No.: 745,931

[22] Filed: Nov. 29, 1976

[51] Int. Cl.$^2$ .................... G01N 27/30; G01N 27/42
[52] U.S. Cl. ............................. 204/195 R; 204/1 T; 204/195 H; 204/272
[58] Field of Search ................ 204/1 T, 1 M, 195 T, 204/195 H, 195 R, 272

[56] References Cited

U.S. PATENT DOCUMENTS

| | | | |
|---|---|---|---|
| 2,651,612 | 9/1953 | Haller | 204/195 R |
| 3,065,156 | 11/1962 | Thompson et al. | 204/195 R X |
| 3,761,377 | 9/1973 | Mang | 204/195 R |
| 3,793,158 | 2/1974 | Hamilton | 204/1 T |
| 3,904,487 | 9/1975 | Lieberman et al. | 204/1 T |

*Primary Examiner*—G. L. Kaplan
*Attorney, Agent, or Firm*—Richard S. Sciascia; Ervin F. Johnston; Thomas Glenn Keough

[57] ABSTRACT

An improvement for an anodic stripping voltammetry system for measuring the presence and concentration of trace metals in a seawater solution yields more representative readings. A combination electrode is fashioned from a porous polyethylene cylinder having a coaxial bore for receiving the flowing solution. A helically extending silver/silver chloride reference electrode is disposed on the outside of the cylinder and a platinum counter electrode is located in its bore. The porous polyethylene prevents chlorides from contaminating the reference electrode while the counter electrode drains off currents. Thus, more representative potential readings between a working electrode and the reference electrode are made as trace metals are stripped away into the circulating solution.

9 Claims, 2 Drawing Figures

4,058,446

ANODIC STRIPPING VOLTAMMETRY SYSTEM AND COMBINATION ELECTRODE ASSEMBLY THEREFORE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Trace metal concentrations in the ocean have recently become of concern because these may be indicative of pollution levels and hence, have an environmental impact. In inshore waters possibly harmful concentrations of trace metals are more common. The sacrificial zinc and lead anodes attached to ships release these metals into the surrounding waters. In some areas, shore installations discharge solutions having cadmium and lead ions into the coastal waters. Anti-fouling paints constantly leach copper which may pose an environmental hazard in poorly flushed bays or shipping lanes having substantial traffic. Thus, in each of these instances, not only is it important to be able to accurately measure the metal concentrations, but it also behooves scientists to be able to understand which chemical forms of these metals are present since the latter determines their toxicity and ultimate disposition of the metals. For example, although copper, zinc, cadmium, and lead are generally released as ions (the toxic form), there are indications that these metals form colloidal hydroxides in the seawater and are removed from solution by agglomeration or precipitation or by absorption or other particulate matter.

Of even more general oceanographic interest is the effect of trace metals on marine primary productivity. It is generally believed that the ionic form of copper even at the low concentrations found in the oceans inhibits the phytoplankton production and that the copper must be first chelated by planktonic exudates before full growth can occur. It is believed that this might explain the low productivity of newly upwelled waters. An investigation therefore, of trace metal concentrations in these areas also is of interest to either validate or disprove a multitude of theories.

The need therefore, is apparent for a technique or system for performing in-situ trace metal analyses which reliably indicates the presence and concentration of metals of interest. One such apparatus has been brought to the state of practical application and is described in U.S. Pat. No. 3,904,487 to Stephen H. Liberman and Alberto Zirino, one of the present coinventors, and entitled "Anodic Stripping Voltammetry and Apparatus Therefor". This apparatus pumps a mercury plating solution through a tubular mercury graphite electrode functioning as a working electrode and a tubular reference electrode. A thin film of mercury is deposited on the inner surface of the working electrode when a plating potential is applied. Next, a seawater sample is pumped through the electrodes and trace metals are reduced onto the mercury film when the plating potential is reconnected. After a predetermined time, a pulsed scanning potential gradient is applied across the two electrodes. At discrete levels within the pulsed scanning potential gradient certain ones of the trace metals are stripped from the active metal film and the magnitudes of the currents at these levels are monitored and recorded. The magnitudes of the currents at the discrete potential levels are proportional to the concentrations of the trace metals, zinc, cadium, lead or copper. The system is reactuated to reintroduce the flowing mercury plating solution through the working electrode to deposit another thin film of mercury. Trace metals are redeposited and stripped from the electrode for successive analyses. Another not so apparent limitation arose by using a reference electrode made of a silver chloride covered silver wire. The silver chloride itself would be stripped into the seawater sample affecting the validity of an analysis. The silver ion tended to obscure the actual concentrations of certain metals of interest. The erosion of the silver ions from preceeding samples affected the subsequent readings. It was found that the silver ion from the reference electrode particularly influenced the copper ion determination to create stability problems for repetitive analyses of several seawater samples. The stability otherwise inherent in a silver electrode was compromised by the current flow through it and the resultant stripping away of the silver ion into the samples. Therefore, there is a continuing need in the state-of-the-art for a more stable reference electrode which helps provide more accurate representations of trace metal concentrations in seawater.

SUMMARY OF THE INVENTION

The present invention is directed to providing an improvement for an anodic stripping voltammetry system for measuring the presence and concentration of trace metals in a seawater sample. Conventional elements include a means for sensing trace metals, a means for feeding the sample solution and a plating solution through the sensing means, a means coupled for alternately coupling the sample solution and the plating solution to the sensing means, a means for depositing a metal plating film on the sensing means while the plating solution is coupled to flow through the sensing means and for reducing trace metals on the metal plating film while the sample solution is alternately coupled to flow through the sensing means, and means for indicating the presence and concentration of trace metals in the sample solution, the improvement including a combination electrode having a tubularly shaped body member provided with a coaxial bore coupled to receive the flow of the plating solution and the sample solution, a reference electrode disposed on the outer surface of the body member, and a counter electrode disposed in the coaxial bore of the body member and reaching to the exterior of the body member, both electrodes extending to the indicating means.

OBJECTS OF THE INVENTION

An object of the invention is to provide an improvement for the anodic stripping voltammetry system.

Another object is to provide a combination electrode electronically cooperating with a working electrode in an anodic stripping voltammetry system.

Yet another object is to provide a combination electrode having a reference electrode and a counter electrode for improved performance.

Still another object is to provide a combination electrode having a tubularly shaped body member to allow the flow of solutions therethrough.

Yet another object is to provide a combination electrode made from a porous body member impregnated with a conducting gel, the gel filled pores allow electrical connection but block the flow of silver ions therethrough.

Yet another object is to provide an electrode having a platinum gauze disposed in the flowing solutions and a helically-extending coil disposed outside the flowing solution, thereby maintaining greater stability.

These and other objects of the present invention will become more readily apparent from the ensuing description when taken together with the drawings.

DESCRIPTION OF THE PREFERRED EMBODIMENT

Figure 1:
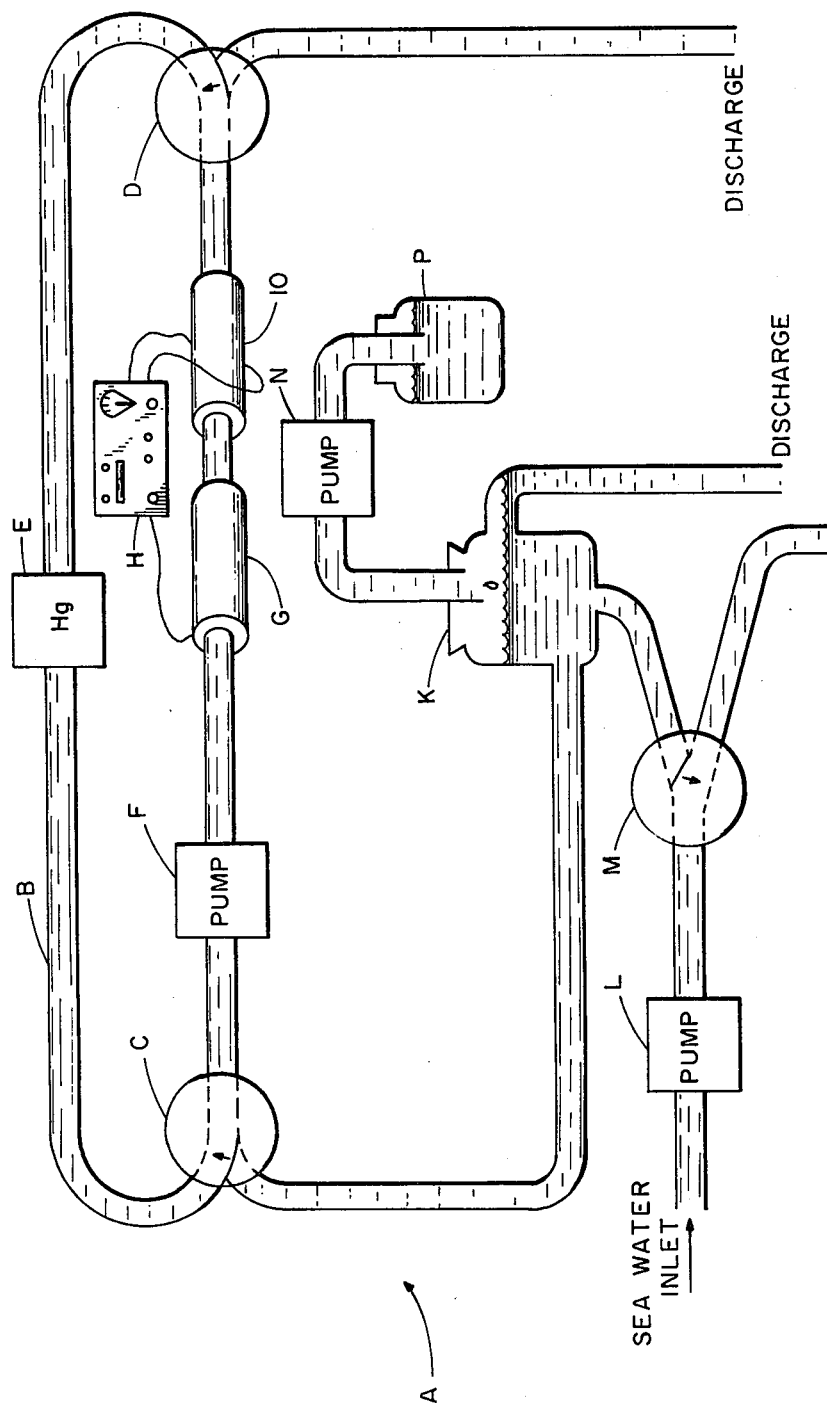
FIG. 1 schematically depicts an anodic stripping voltammetry system including the improved combination electrode.
Figure 2:
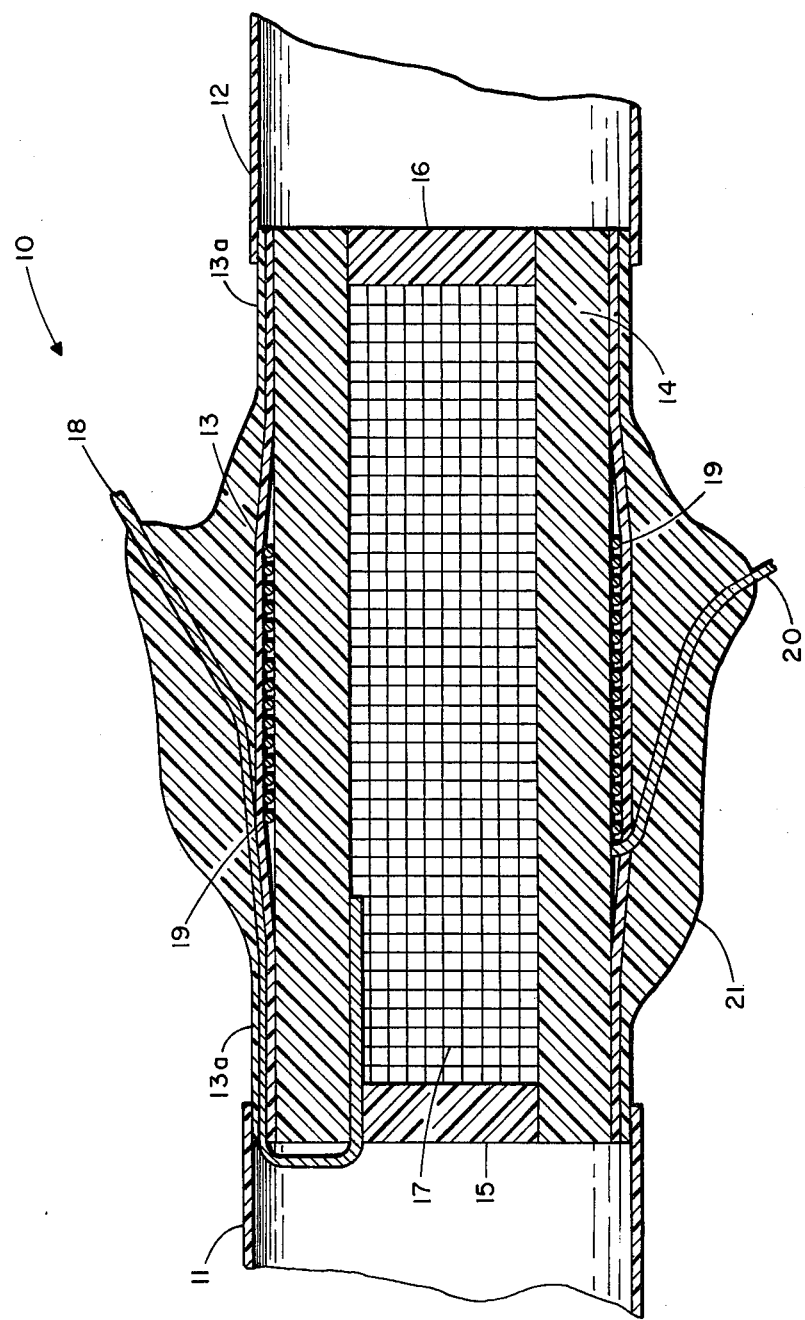
FIG. 2 is a longitudinal cross-sectional view of the combination electrode.

The anodic stripping voltammetry process has demonstrated a capability for determining the presence and concentration of trace metals in various solutions. The system of the patent identified above was found to be particularly capable of making accurate trace metal analysis in seawater with manual switching of the sample solution and the plating solution through the tubular graphite-mercury electrode and its reference electrode. This system was modified to incorporate automatic switching of the stop cocks; however, the seawater samples still were kept in containers that needed to be changed when another sample was to be analyzed.

The improved system A of this invention allows for the continuous drawing in of seawater samples and the automated analysis thereof. The analytical procedure is substantially the same as that disclosed in the specified patent and a detailed reiteration is felt to be unnecessary. However, a brief description of this system's operation will follow to help focus on the significant improvements afforded by combination electrode 10.

The system includes a closed plating loop or circuit B when valves C and D are switched appropriately. A container E of an active metal plating solution, mercuric nitrate, is in circuit B for allowint the depositing of a thin film of mercury on a working electrode G as the plating solution is pumped through it by a pump F. A typical merucry plating solution is a mercuric nitrate solution of about 1 or 2 $\times$ 10$-$5 M which has been found to be satisfactory for depositing a suitable film on working electrode G.

The working electrode is a tubular mercurygraphite electrode substantially identical to the one described in U.S. Pat. No. 3,905,487. When suitable potentials are applied to the electrode from an interconnected polarographic analyzer H, a thin film of mercury is deposited on its inner surface. Potentials in the neighborhood of approximately $-1.4$V with respect to the potential on the combination electrode 10 will effect depositing of the film. The polarographic analyzer chosen for the anodic stripping voltammetry operation is a well known commercially available unit identified in the scientific community as a Princeton Applied Research Model 174. Appropriate circuitry and connections routinely are made for this operation.

After a thin film has been deposited on the working electrode G, seawater is pumped in by a pump L and fed to a reservoir K via a valve M. An overflow duct from the reservoir allows the discharge of excessive amounts of the seawater sample.

When valves C and D are actuated to link the reservoir to circuit B, seawater is pumped by pump F through working electrode G and combination electrode 10. A given amount of the seawater sample is analyzed only once and it is purged from circuit B when valve D is switched to discharge the seawater sample. A standard solution P is periodically introduced into the reservoir K by a pump N to allow a comparison by a polographic analyzer H between the known concentration of trace metals of interest in standard solution P and to the unknown concentration of the trace metals in the seawater samples.

As mentioned before, the tubular mercury graphite electrode is essentially as described in the cited patent. The mercury plating solutions and the standard solutions are also within the same parameters as described in the patent. The tubing forming the closed loop as well as the inlets bringing in the seawater samples are within the state of the art and are fabricated from materials which will not contaminate any of the solutions.

Briefly, the analysis procedure is as follows: Pump L is continuously operating and when valve M is appropriately switched, seawater is brought into reservoir K and the overflow is discharged. Although not shown in the drawing, the seawater sample is purged of oxygen in the reservoir with Coleman grade carbon dioxide to bring the pH of the seawater to about 4.9. The height of the discharge port in reservoir K controls the sample volume contained and the volume of the flow of the sample into the reservoir determines the degree of rinsing of the reservoir. When a sample has been collected in the reservoir, valve M is switched and the seawater flow is diverted to discharge.

The mercuric nitrate plating solution from container E is circulated through the working electrode G and the combination electrode 10. As mentioned before, the potential for deposition of the mercury on the electrode G is $-1.4$ volts with respect to the potential at combination electrode 10.

Valves C and D are switched to feed the seawater sample through electrodes G and 10. After a period of approximately four minutes during which a potential of at least $-1.4$ volts is applied between electrodes, zinc, cadmium, lead and copper ions are deposited on electrode G. The flow through the electrodes is stopped and a pulsed potential ramp of increasing positive magnitude is fed to electrode G for a period of time, usually in the neighborhood of 4 minutes. The resulting ionic currents due to the oxidation of the metal ions are monitored and their magnitudes recorded. Laboratory experiments have verified that magnitude of the current is proportional to the concentrations in the seawater sample of zinc, cadmium, lead and coppper, respectively. A chart recorder or other suitable instrumentation is connected to the polarographic analyzer for collecting the data.

After the trace metals have been stripped from the active working electrode back into solution, the mercuric nitrate solution is reintroduced to deposit another active metal film and another seawater sample, with or without a standard solution addition, is fed through the electrodes. This process can be manual or fully automated, depending on the resources at hand.

The improvement to this system or for that matter, to the system of the cited patent, is in the combination electrode 10 itself. This electrode is interposed in the circuit B between plastic tubing sections 11 and 12. A piece of heat shrink tubing 13 is covered along annular surfaces 13a by the plastic tubing sections to maintain a fluid tight coupling of the electrode to the rest of the system.

A 2.5 centimeter cylinder of porous, polyethelyne tubing 14 functions as the body member of the combination electrode and it has a 0.32 centimeter inner diameter and a 0.64 centimeter outer diameter. The polyethelyne has a porosity of about sixty microns. Openings 15 and 16 at opposite ends of a coaxial bore permit the flow of the plating solution and the sample solution through the combination electrode.

A piece of plantinum gauze or counter electrode is disposed in the coaxial bore and does not overly restrict the flow of the solutions through the electrode. A length of platinum foil 18 is electrically connected to the platinum gauze and extends outwardly from the electrode.

A coil 19 of annodized silver wire covered with silver chloride is wrapped about the cylinder of porous polyetheylene and its silver lead 20 reaches away from the cylinder. The heat shrink tubing 13, in addition to preventing contaminants from reaching the electrode, holds the coil 19 closely against the outer surfaces of the porous polyetheylene cyliner.

The porous polyethylene tube having a porosity of approximately 60 microns was impregnated with potassium chloride saturated agar. The impregnation was facilitated by immersing the tube in the warm agar solution under a vacuum.

Finally, the electrode was potted in epoxy 21 to orient leads 18 and 20. The potting also increased the structural integrity of the electrode.

After the silver wire and the platinum foil were fixed in place with the epoxy adhesive, the bare silver wire was soldered on the reference connection of the Princeton Applied Research, Model 174, polarographic analyzer and the platinum foil was soldered to the corresponding counter connection. The obvious advantages, of course, of having the silver wire coupled to the reference lead of the analyzer and the platinum foil coupled to the counter connection of the analyzer is that the current is removed by the platinum foil 17. Potential readings between the working electrode G with respect to the reference silver lead 20 are not affected by the current. Current otherwise oxidizes the silver electrode. Cylinder 14 with its 60 micron porosity does not permit oxidation of the silver wire so that potential readings between the working electrode G and the reference leads 19 are stabilized. Current is bled off to the analyzer through the platinum gauze and its associated lead 18 so that potential readings are not affected by current flow caused by the stripping away of trace metals from the seawater sample solutions.

Obviously, many modifications and variations of the present invention are possible in the light of the above teachings, and, it is therefore understood that within the scope of the disclosed inventive concept, the invention may be practiced otherwise than as specifically described.

What is claimed is:

1. In an anodic stripping voltammetry system for measuring the presence and concentration of trace metals in a sample solution having a source of a metal plating solution, a means for sensing trace metals, a means for feeding the sample solution and the plating solution through the sensing means, a means coupled for alternately coupling the sample solution and the plating solution to the sensing means, a means for depositing a metal plating film on the sensing means while the plating solution is coupled to flow through the sensing means and for reducing trace metals on the metal plating film while the sample solution is alternately coupled to flow through the sensing means, and means for indicating the presence and concentration of trace metals in the sample solution, an improvement therefor is provided comprising:

a combination electrode including a tubularly shaped body member provided with a coaxial bore coupled to receive the flow of the plating solution and the sample solution, a reference electrode disposed on the outer surface of the body member, and a counter electrode disposed in the bore of the body member and reaching to the exterior of the body member both electrodes extending to the indicating means.

2. An improvement according to claim 1 wherein the tubularly shaped body member is fashioned from a porous polyethylene tube impregnated with a potassium chloride saturated agar solution and the reference electrode is a helically extending length of anodized wire covered wih silver chloride.

3. An improvement according to claim 2 further including:

a section of heat shrink tubing extending to contain the tubularly shaped body member and to hold the helically extending length of anodized wire against the outer surface of the body member.

4. An improvement according to claim 3 in which the counter electrode is platinum gauze disposed in the coaxial bore coupled to a platinum foil strip reaching to the exterior of the body member.

5. An improvement according to claim 4 further including:

an epoxy seal potting the tubularly shaped body member, the helically extending length of anodized wire and the heat shrink tubing therein.

6. A combination electrode for receiving a flowing solution therethrough comprising:

a tubularly shaped body member fashioned from a porous polyethylene tube impregnated with a potassium chloride saturated agar solution and provided with a coaxial bore coupled to receive the flowing solution;

a reference electrode in the form of a helically extending length of anodized wire covered with silver chloride disposed on the outer surface of the body member and a counter electrode disposed in the coaxial bore of the body member and reaching to the exterior of the body member.

7. A combination electrode according to claim 6 further including:

a section of heat shrink tubing extending to contain the tubularly shaped body member and to hold the helically extending length of anodized wire against the outer surface of the body member.

8. A combination electrode according to claim 7 in which the counter electrode is platinum gauze disposed in the coaxial bore coupled to a platinum foil strip reaching to the exterior of the body member.

9. A combination electrode according to claim 8 further including:

an epoxy seal potting the tubularly shaped body member, the helically extending length of annodized wire and the heat shrink tubing therein.

* * * * *